US010022736B2

(12) United States Patent
Michienzi

(10) Patent No.: US 10,022,736 B2
(45) Date of Patent: Jul. 17, 2018

(54) REUSABLE FITTING FOR ATTACHING A CONDUIT TO A PORT

(75) Inventor: Joseph D. Michienzi, Plainville, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 1037 days.

(21) Appl. No.: 14/232,711

(22) PCT Filed: Aug. 23, 2012

(86) PCT No.: PCT/US2012/051981

§ 371 (c)(1), (2), (4) Date: Jan. 14, 2014

(87) PCT Pub. No.: WO2013/032835

PCT Pub. Date: Mar. 7, 2013

(65) Prior Publication Data

US 2014/0152003 A1 Jun. 5, 2014

Related U.S. Application Data

(60) Provisional application No. 61/527,747, filed on Aug. 26, 2011, provisional application No. 61/527,639, (Continued)

(51) Int. Cl.
*B05B 5/16* (2006.01)
*B01D 15/10* (2006.01)
(Continued)

(52) U.S. Cl.
CPC ................ *B05B 5/16* (2013.01); *B01D 15/10* (2013.01); *B01D 15/22* (2013.01); *G01N 30/60* (2013.01);
(Continued)

(58) Field of Classification Search
CPC ........ B01D 15/10; B01D 15/14; B01D 15/22; B01D 15/1871; G01N 30/6039;
(Continued)

(56) References Cited

U.S. PATENT DOCUMENTS 4,083,702 A * 4/1978 Hartigan ............ G01N 30/6039
4,619,473 A * 10/1986 Someya ................ B01D 15/08 285/353 X (Continued)

FOREIGN PATENT DOCUMENTS

CN 1867388 A 11/2006
CN 101495763 A 7/2009

(Continued)

OTHER PUBLICATIONS

International Preliminary Report on Patentability in counterpart international patent application No. PCT/US12/51981, dated Mar. 13, 2014; 7 pages.

(Continued)

*Primary Examiner* — Greg Binda
*Assistant Examiner* — Zachary T Dragicevich
(74) *Attorney, Agent, or Firm* — Schmeiser, Olsen & Watts LLP; William G. Guerin

(57) ABSTRACT

Described is a reusable fitting for attaching a conduit to a port. The fitting includes a housing, a spring, a retainer and a cap. The retainer is capable of locking and unlocking a conduit in the fitting. The fitting provides a high pressure fluid-tight seal and a substantially zero void volume at the junction of two fluidic conduits. The fitting is removable, reusable and replaceable, and allows a user to make and remake connections of a capillary to a fluidic port without permanently binding a ferrule to a specific capillary and thus to a specific port. The fitting can be replaced if part or all of the fitting is damaged during use.

17 Claims, 4 Drawing Sheets

Related U.S. Application Data filed on Aug. 26, 2011, provisional application No. 61/527,648, filed on Aug. 26, 2011, provisional application No. 61/527,638, filed on Aug. 26, 2011, provisional application No. 61/621,852, filed on Apr. 9, 2012.

(51) Int. Cl.

| | |
|---|---|
| ***G01N 30/60*** | (2006.01) |
| ***B01D 15/22*** | (2006.01) |
| *B01D 15/18* | (2006.01) |
| *G01N 30/72* | (2006.01) |

(52) U.S. Cl.

CPC ....... *G01N 30/603* (2013.01); *G01N 30/6026* (2013.01); *G01N 30/6052* (2013.01); *B01D 15/1871* (2013.01); *G01N 30/6004* (2013.01); *G01N 30/6039* (2013.01); *G01N 30/6095* (2013.01); *G01N 30/7266* (2013.01); *Y10T 29/49908* (2015.01)

(58) Field of Classification Search

CPC ........... G01N 30/6052; G01N 30/7266; G01N 30/60395; G01N 30/6004; G01N 30/6026; G01N 30/60; G01N 30/603; G01N 30/6095; B05B 5/16; Y10T 29/49908

USPC ................................ 285/246, 255, 353, 354

See application file for complete search history.

(56) References Cited

U.S. PATENT DOCUMENTS

| | | | | |
|---|---|---|---|---|
| 5,163,722 | A | 11/1992 | Worden | |
| 5,234,235 | A | 8/1993 | Worden | |
| 5,595,406 | A | 1/1997 | Warchol | |
| 5,601,785 | A * | 2/1997 | Higdon | G01N 30/6039 210/198.2 |
| 6,095,572 | A * | 8/2000 | Ford | F16L 37/107 210/198.2 |
| 6,193,286 | B1 | 2/2001 | Jones et al. | |
| 6,494,500 | B1 | 12/2002 | Todosiev et al. | |
| 9,314,791 | B2 * | 4/2016 | Kim | |
| 2009/0189390 | A1 | 7/2009 | Blassman et al. | |
| 2009/0295156 | A1 * | 12/2009 | Ford | G01N 30/6026 285/384 |
| 2010/0224543 | A1 | 9/2010 | Ellis et al. | |
| 2013/0298647 | A1 * | 11/2013 | Falk-Jordan | G01N 30/6026 285/99 |

FOREIGN PATENT DOCUMENTS

| | | | |
|---|---|---|---|
| DE | 102008059897 | A1 | 6/2010 |
| EP | 2071223 | A1 | 6/2009 |
| JP | 09-317971 | A | 12/1997 |
| JP | 10-170490 | A | 6/1998 |
| WO | 2010102194 | A1 | 9/2010 |

OTHER PUBLICATIONS

Notice of Rejection in counterpart Japanese Patent Application No. 2014-527283, dated May 24, 2016; 4 pages.

International Search Report and Written Opinion in related international patent application No. PCT/US12/51981, dated Aug. 23, 2012; 9 pages.

Extended Search Report in counterpart European Patent Application No. 12828696.0, dated Mar. 31, 2015; 6 pages.

First Office Action in counterpart Chinese Patent Application No. 201280041112.0, dated Dec. 31, 2014; 25 pages.

* cited by examiner

REUSABLE FITTING FOR ATTACHING A CONDUIT TO A PORT

RELATED APPLICATIONS

This application claims the benefit of the earlier filing date of U.S. Provisional Patent Application Ser. No. 61/527,638, filed Aug. 26, 2011 and titled "Reusable Fitting for Attaching a Conduit to a Port," U.S. Provisional Patent Application Ser. No. 61/527,639, filed Aug. 26, 2011 and titled "Chromatography Apparatus with Diffusion-Bonded Coupler," U.S. Provisional Patent Application Ser. No. 61/527,747, filed Aug. 26, 2011 and titled "Liquid-Chromatography Conduit Assemblies Having High-Pressure Seals," U.S. Provisional Patent Application Ser. No. 61/527,648, filed Aug. 26, 2011 and titled "Electrospray Assembly for a Microfluidic Chromatography Apparatus," and U.S. Provisional Patent Application Ser. No. 61/621,852, filed Apr. 9, 2012 and titled "Chromatography Column Assembly," the entireties of which are incorporated herein by reference.

FIELD OF THE INVENTION

The invention relates generally to a reusable fitting for attaching a conduit to a port. More particularly, some embodiments of the invention relate to a removable and replaceable fitting for use in high pressure fluidic systems such as high performance liquid chromatography (HPLC) systems.

BACKGROUND

A capillary HPLC system typically requires a steel ferrule to connect a capillary to a metal or plastic fluidic port to provide a fluid-tight seal and a substantially zero void volume between the capillary and a conduit embedded within the port. In such a connection, the capillary is held in a fitting having the steel ferrule and a compression nut. The compression nut presses on the ferrule so that the fitting grips the capillary and so the capillary is pressed into direct contact with an inlet or an outlet of the conduit embedded in the port. Once the connection is made, the steel ferrule is permanently secured to the capillary and therefore only usable with a specific port. If the fitting is moved to a different port, even small manufacturing tolerances generally result in either a void volume or an interference which can cause damage and/or cause the steel ferrule to be improperly seated. Moreover, because of the permanent attachment of the steel ferrule to the capillary, if a portion of the fitting is damaged during use, the entire fitting is discarded and a new one installed because any portion of the fitting cannot be simply removed or replaced.

As known in the art, there are alternatives to non-removable, non-reusable and non-replaceable steel ferrules for use in HPLC systems, such as polytetrafluoroethylene ferrules and high performance polyetheretherketone fittings. However, polytetrafluoroethylene ferrules are limited to pressures below a few thousand pounds per square inch (psi), and high performance polyetheretherketone fittings have limited reusability as the polyetheretherketone sealing cone can be damaged from continual use.

SUMMARY

In one aspect, the invention features a reusable fitting for attaching a conduit to a port. The reusable fitting includes a housing, a spring, a retainer and a cap. The housing includes a ferrule portion at a proximal end of the housing. The spring is in physical communication with the housing. The retainer is disposed between the spring and the housing. The retainer has an opening for admitting a distal portion of a conduit and a retention feature fixed to a proximal end of the conduit to limit axial movement of the conduit in a distal direction. The retainer defines an off-center opening for passing the retention feature of the conduit. The cap is in communication with the spring to urge the spring against the retainer to thereby urge the conduit in a proximal direction.

In another aspect, the invention features a liquid chromatography device that includes a conduit for communicating a fluid, a port in fluid communication with the conduit, and a fitting for attaching the conduit to the port. The fitting includes a housing having a ferrule portion at a proximal end of the housing and a spring in physical communication with the housing. The fitting also includes a retainer and a cap. The retainer is disposed between the spring and the housing. The retainer has an opening for admitting a distal portion of the conduit and is in physical communication with a retention feature fixed to a proximal end of the conduit to limit axial movement of the conduit in a distal direction. The retainer defines an off-center opening for passing the retention feature of the conduit. The cap is in physical communication with the spring to urge the spring against the retainer so that the retainer urges the conduit in a proximal direction.

In yet another aspect, the invention features a kit having component parts capable of being assembled to form a reusable fitting for attaching a conduit to a port. The reusable fitting includes a housing having a ferrule portion at a proximal end of the housing. The reusable fitting also includes a spring in physical communication with the housing and a retainer disposed between the spring and the housing, and a cap. The retainer has an opening for admitting a distal portion of a conduit and is in physical communication with a retention feature fixed to a proximal end of the conduit to limit axial movement of the conduit in a distal direction. The retainer defines an off-center opening for passing the retention feature of the conduit. The cap is in physical communication with the spring to urge the spring against the retainer so that the retainer urges the conduit in a proximal direction.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

DETAILED DESCRIPTION

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

The present teaching will now be described in more detail with reference to exemplary embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure as described herein.

The term "substantially", as used herein, may be applied to modify any quantitative representation which could permissibly vary without resulting in a change in the basic function to which it is related.

The term "capillary", as used herein, refers to tubes having an inner diameter that does not exceed about 300 μm. Depending on context, the words "capillary" and "conduit" are used interchangeably herein.

The term "retention feature" as used herein refers to anything constructed or configured on a conduit that limits the axial movement of a conduit when held in a fitting.

In brief overview, the invention relates to a fitting comprising, in part, a ferrule, formed of polyetheretherketone or the like, and a retainer that is capable of locking and unlocking a conduit in the fitting. The fitting provides a fluid-tight seal and a substantially zero void volume at the junction of two fluidic conduits at high pressures that in some embodiments may exceed 20,000 psi. The fitting is removable, reusable and replaceable, and allows a user to make and remake connections of a capillary to a fluidic port without permanently binding a ferrule to a specific capillary and thus to a specific port. The fitting can be replaced if part or all of the fitting is damaged during use.

Figure 1:
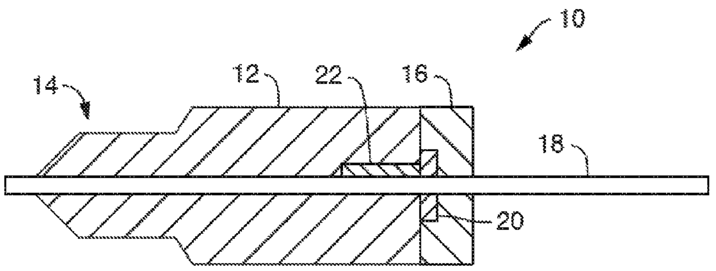
FIG. 1 is a diagram of an embodiment of a reusable fitting in accordance with the invention.

FIG. 1 is a diagram of a reusable fitting 10 that includes a housing 12, having a ferrule portion 14, and a retainer 16. The ferrule portion 14 has a bore defining a passage for receiving a conduit 18 and is configured to be received by a female receptacle of a metal or plastic port. The ferrule portion 14 is formed, for example, of polyetheretherketone or a polyetheretherketone-type polymer. The ferrule portion 14 can be integral with the housing 12, as shown, or may be a separate piece.

The conduit 18 is held in the fitting 10 and is pressed into the receptacle to mate with the inlet or outlet of a conduit embedded in the port. The compression can be achieved using any suitable force exerted on the ferrule portion 14, such as screw compression force, spring force, clamping force, or combination of one or more of these forces, while allowing for the conduit 18 to be detached from the ferrule portion 14 at a later time without being damaged. In other words, the ferrule portion 14 is not permanently attached to the conduit by the compression.

The word "retainer", as used herein, means any object having a structure that enables the conduit 18 to be locked to the fitting or unlocked from the fitting. The retainer 16 can be a portion of the housing 12 or may be a separate piece positioned either inside or outside of the housing 12. The retainer 16 has an opening aligned with the passage defined by the ferrule portion 14 for receiving the conduit 18. The retainer 16 includes one or more locking regions 20 or mechanisms. By way of examples, a locking region 20 can engage one or more hooks, bands, slots, grooves, pins, flanges or similar features. A locking region 20 can lock the conduit 18 by coupling a retention feature 22 of the conduit 18 into the locking region. In addition, the structure 20 can unlock the conduit 18 by allowing the retention feature 22 to bypass the impediment imposed by the locking region 20. In various embodiments, the retention feature 22 associated with the conduit 18 is a steel sheath disposed on a portion of the conduit 18, a material coated on a surface of the conduit 18, or anything configured or shaped on the conduit 18 that can interface with the locking region 20 to limit axial movement of the conduit 18 within the fitting 10.

Figure 2:
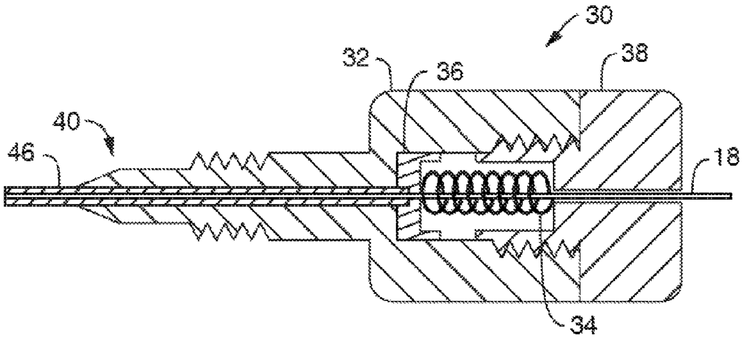
FIG. 2 is a cross-sectional view of an embodiment of a reusable fitting in accordance with the invention.

FIG. 2 is a cross-sectional view of one embodiment of a reusable fitting 30 in accordance with the invention. The fitting 30 includes a housing 32, a spring 34, a retainer 36 and a cap 38. The housing 32 is shown separately in FIG. 3 and includes a ferrule portion 40 at the proximal end and an interior surface 42 that defines a chamber 43 at the distal end. A housing can have any suitable shape, for example, the illustrated housing 32 has a circular cross-section although other polygonal cross-sectional shapes are possible. The housing 32 is fabricated from any suitable material such as polymeric material or metallic material. Although shown as a one-piece housing 32, in some alternative embodiments the housing includes two or more pieces. In other embodiments, the ferrule portion 40 can be a separate piece from the remainder of the housing 32. The illustrated ferrule portion 40 has a bore 44 that defines a passage for receiving a conduit. In some embodiments the inner diameter of the bore 44 does not exceed about 300 μm. The width (or diameter) of the chamber 43 is greater that the width (or diameter) of the bore 44. The ferrule portion 40 is configured in shape and size to be compatible with a female receptacle of a port such that the ferrule portion 40 can be tightened into the port. The ferrule portion 40 is formed of polyetheretherketone or from similar materials such as a polyetheretherketone-type polymer although in other embodiments the ferrule portion 40 may be comprised of other materials such as graphite or polyimide.

Figure 3:
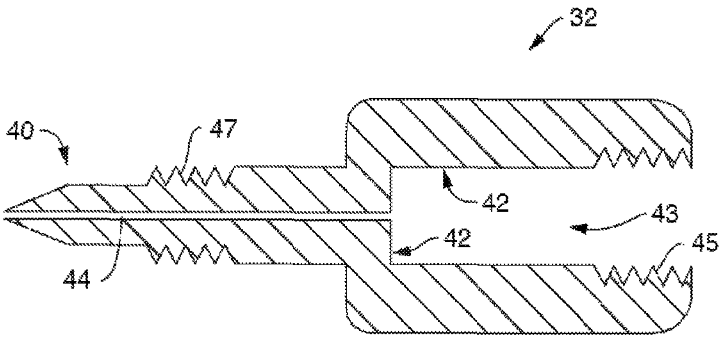
FIG. 3 is a cross-sectional view of the housing for the reusable fitting of FIG. 2.

Referring to both FIG. 2 and FIG. 3, the spring 34 is disposed in the chamber 43 of the housing 32. The retainer 36 is disposed inside the chamber 43 at an end nearest to the ferrule portion 40. The housing 32 has a threaded interior surface 45 that engages a threaded surface on the cap 38 and a threaded exterior surface 47 near the ferrule portion 40 that is configured for attachment to a port. The spring 34 is disposed in the chamber 43 between the retainer 36 and the cap 38. By way of examples, the spring 34 can be a helical spring (as shown), a spring leaf, a compressible resilient washer, a hollow cylinder formed of compressible material and the like, such that when the spring 34 is under compression between the retainer 36 and cap 38, a force is applied to keep the retainer 36 secured in place within the chamber 43 of the housing 32. Consequently, the retainer 36 urges the conduit 18 in a proximal direction (i.e., to the left in the figures).

In some preferred embodiments, the retention feature comprises a sleeve 46 that is disposed on the proximal portion of the conduit 18. The sleeve 46 engages the structure of the retainer 36 to limit the axial movement of the conduit 18 in a distal direction (i.e., to the right in the figures).

In one embodiment, the housing 32 does not include a ferrule portion 40 as shown in FIG. 2. Instead, a replaceable cap is provided at the end of the proximal portion of the conduit or sleeve. By way of example, the cap can be fabricated from a polyetheretherketone-type polymer and shaped to be held at the end of the conduit or sleeve. As the fitting is urged into a receptacle to couple the conduit to a port, the compression of the spring applies sufficient axial force to provide a face seal at the endface of the conduit. In another alternative embodiment, a replaceable gasket is used in place of the cap to seal the endface of the conduit to the port within the receptacle. The cap or the gasket can be removed and optionally replaced with another cap or gasket when the fitting is reattached to the receptacle or secured to a port in a different receptacle.

Figure 4A:
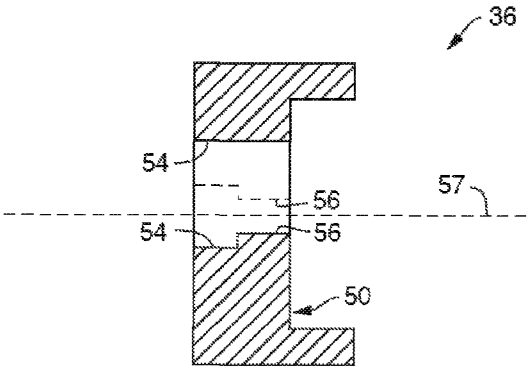
FIG. 4A is a cross-sectional side view of the retainer for the reusable fitting of FIG. 2.
Figure 4B:
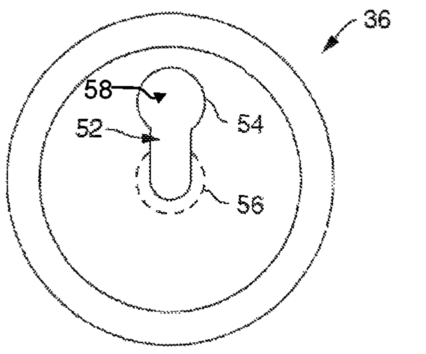
FIG. 4B is an end view of the retainer shown in FIG. 4A.

FIG. 4A is a cross-sectional side view of the retainer 36 for the reusable fitting 30 of FIG. 2 and FIG. 4B is an end view of the retainer 36 corresponding to looking in a direction from left to right in FIG. 4A. The retainer 36 includes an inner surface 50 at one end to receive one end of the spring 34 and a slot 52 at the other end that is aligned with the passage in the ferrule portion of the housing for receiving the conduit. The slot 52 includes a first inner surface 54 having a perimeter and a second inner surface 56 that has a perimeter that is less than the perimeter of the first inner surface 54. The locking region is defined by the combination of the inner surfaces 54 and 56. The first inner surface 54 defines an opening that is sufficient to accept the sleeve (retention feature) on the conduit while the second inner surface 56 has the smaller perimeter that cannot accept the sleeve but is still sufficient to allow the conduit to pass.

The unlocking region is defined by the off-center opening 58 at one end of the slot 52. The off-center opening 58 is a radial extension for both inner surfaces 54 and 56 that allows the proximal portion of the conduit that includes the sleeve to pass through the retainer 36 by bypassing the impediment presented by the locking region defined by the second inner surface 56. When the conduit and sleeve are moved radially toward the center of the retainer 36 (i.e., toward axis 57), axial motion in a distal direction is prevented once the sleeve encounters the narrow opening defined by the second inner surface 56.

The larger diameter opening at the end of the slot 52 that is furthest from the axis 57 allows a user to pass the retention feature 46 through the retainer 36 and then to move the retention feature 46 and conduit 18 back to lie along the axis 57 to thereby lock the retention feature 46 and the conduit 18 to the fitting 30. The retention feature 46 and conduit 18 can subsequently be detached removed from the fitting 30 in a distal direction without being damaged. The fitting 30 can be reused with another conduit in the same port or may be used for coupling a conduit to a different port. In other embodiments, slots of other shapes and sizes can be used to lock the retention feature 46 and conduit 18 to a fitting.

Figure 5:
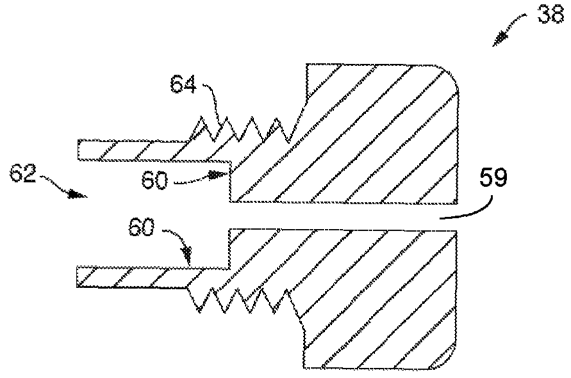
FIG. 5 is a cross-sectional view of the cap for the reusable fitting of FIG. 2.

FIG. 5 shows a cross-sectional view of the cap 38 for the reusable fitting 30 of FIG. 2. The cap 38 has a bore 59 aligned with the passage defined by the ferrule portion 40 of the housing 32 of FIG. 3, and an inner surface 60 at its proximal end defining a cavity 62 for engaging the spring. An exterior surface of the cap 38 includes threads 64 to engage complimentary threads 45 in the chamber 43 of the housing 32 of FIG. 3. Referring again to FIG. 2, the cap 38 is tightened into the housing 32 by rotation which urges the spring 34 against the retainer 36. In turn, the retainer 36 urges the ferrule portion 40 to seal against a fluidic port.

In one embodiment of the invention, the component parts of a reusable fitting, such as the fitting 30 of FIG. 2, are provided as a kit. The component parts are capable of being assembled to form a reusable fitting for attaching a conduit to a port.

Figure 6A:
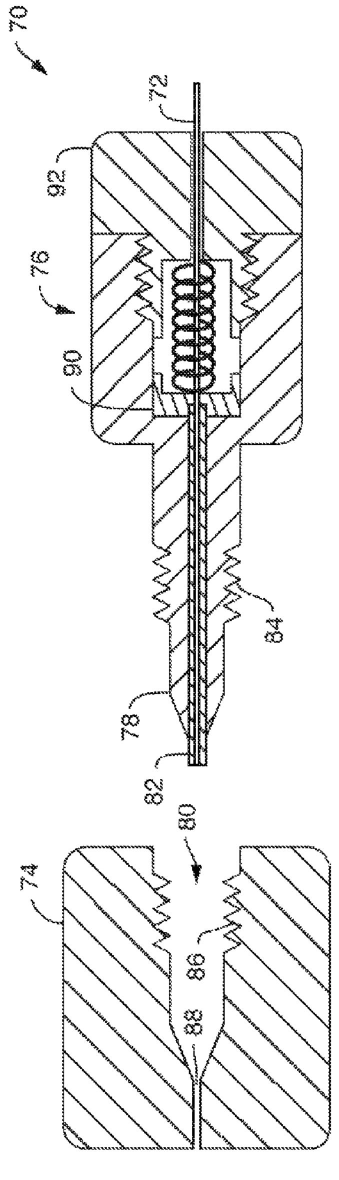
FIG. 6A is a cross-sectional illustration of a portion of an embodiment of a liquid chromatography device in a decoupled configuration in accordance with the invention.
Figure 6B:
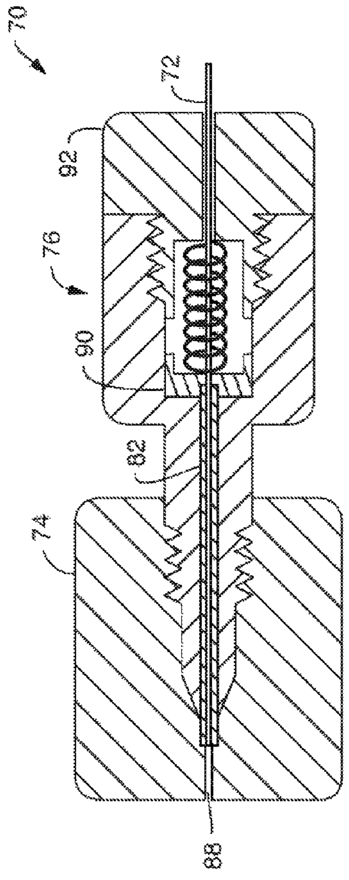
FIG. 6B is a cross-sectional illustration of a coupled configuration for the portion of the liquid-chromatography device shown in FIG. 6A.

FIG. 6A and FIG. 6B are cross-sectional diagrams of a portion of a liquid chromatography device 70 in a decoupled configuration and coupled configuration, respectively, in accordance with one embodiment of the invention. The illustrated portion 70 includes a conduit 72 for communicating a fluid, a port 74 for fluid communication with the conduit 74, and a fitting 76. For example, the conduit 72 and the fitting 76 can be similar to the conduit 18 and fitting 30 shown in FIG. 2. The port 74 can be a fluidic inlet port or a fluidic outlet port, for example, an output port of a pump, an input port of a column, a sample injector port, a port of a valve, or a port of a flow splitter tee. For example, the port 74 can be fabricated from metal or plastic. The fitting 76 includes a ferrule portion 78 having a shape and a size compatible with the female receptacle 80 of the port 74 such that the ferrule portion 78 can be tightened into the port 74.

By way of non-limiting numerical examples, the conduit 72 can have an inner diameter of less than or approximately 300 μm. A portion of the conduit 72 is typically disposed within a sleeve 82 that extends through the ferrule portion 78 of the fitting 76.

A threaded portion 84 of the fitting 76 mates with a threaded portion 86 of the female receptacle 80 of the port 74. When tightened into the port 74 by the matting threads, the fitting 76 presses the conduit 72 forward and against the inlet/outlet of a conduit 88 embedded in the port 74. In turn, the conduit 72 urges the retainer 90 backwards toward the cap 92. The device 70 provides a fluid-tight seal and a substantially zero void volume at the joint of the two conduits 72 and 88, and can withstand pressures that may exceed 20,000 psi.

In some embodiments, the liquid chromatography device is a HPLC system, for example, a version of an ACQUITY UPLC® system or nanoACQUITY UPLC® system available from Waters Corporation of Milford, Mass.

Modifications, alterations, and other implementations of what is described herein will occur to those of ordinary skill in the art without departing from the teaching of the invention as claimed. For example, various embodiments include a spring in the form of a coil, springs of other structural forms are contemplated. For example, the spring can be any structure or mechanism that has a spring constant or other elastic properties, such as a wave washer, elastomeric material and the like. Accordingly, the invention is not limited to the preceding illustrative descriptions.

What is claimed is:

1. A reusable fitting for attaching a conduit to a port, comprising:
- a housing comprising a chamber and a ferrule portion at a proximal end of the housing;
- a spring disposed inside the chamber;
- a retainer disposed inside the chamber between a first end of the spring and the housing, the retainer formed as a single integral body and having a first opening for admitting a distal portion of a conduit and for admitting a retention feature fixed to a proximal end of the conduit to limit axial movement of the conduit in a distal direction, the retainer having an inner surface at a distal end of the retainer configured to engage the first end of the spring and having a slot at a proximal end of the retainer, a portion of the slot being aligned with the passage defined by the ferrule portion of the housing for receiving the conduit, the slot having a first inner surface that defines the first opening to receive the retention feature and a second inner surface that defines a second opening that is smaller than the first opening and sized to pass the conduit and impede the retention feature, the slot further including an off-center opening which is a radial extension in relation to the first and second inner surfaces; and a cap attached to a distal end of the housing and engaging a second end of the spring to urge the spring against the retainer to thereby urge the conduit in a proximal direction.

2. The fitting of claim 1 wherein the ferrule portion has a bore defining a passage for receiving a conduit.

3. The fitting of claim 2 wherein the chamber has a width greater than the bore of the ferrule portion.

4. The fitting of claim 1 wherein at least a portion of the chamber is internally threaded.

5. The fitting of claim 4 wherein a surface of the cap is threaded for engaging the internally threaded portion of the chamber to enable the cap to be tightened to the housing.

6. The fitting of claim 1 wherein the ferrule portion is formed of polyetheretherketone.

7. The fitting of claim 1 wherein the housing is formed of polymer or steel.

8. The fitting of claim 1 wherein an exterior surface of the housing is threaded for attachment to a port.

9. The fitting of claim 1 wherein the retention feature comprises a sleeve disposed on the proximal portion of the conduit.

10. The fitting of claim 9 wherein the sleeve is formed of steel.

11. A liquid-chromatography device, comprising:

a conduit for communicating a fluid;

a port in fluid communication with the conduit; and a fitting for attaching the conduit to the port, the fitting comprising:

a housing comprising a chamber and a ferrule portion at a proximal end of the housing;

a spring disposed inside the chamber;

a retainer disposed inside the chamber between a first end of the spring and the housing, the retainer formed as a single integral body and having a first opening for admitting a distal portion of a conduit and for admitting a retention feature fixed to a proximal end of the conduit to limit axial movement of the conduit in a distal direction, the retainer having an inner surface at a distal end of the retainer configured to engage the first end of the spring and having a slot at a proximal end of the retainer, a portion of the slot being aligned with the passage defined by the ferrule portion of the housing for receiving the conduit, the slot having a first inner surface that defines the first opening to receive the retention feature and a second inner surface that defines a second opening that is smaller than the first opening and sized to pass the conduit and impede the retention feature, the slot further including an off-center opening which is a radial extension in relation to the first and second inner surfaces; and a cap attached to a distal end of the housing and engaging the second end of the spring to urge the spring against the retainer to thereby urge the conduit in a proximal direction.

12. The liquid-chromatography device of claim 11 wherein an exterior surface of the housing is threaded for attachment to the port.

13. The liquid-chromatography device of claim 11 wherein the ferrule portion is formed of polyetheretherketone.

14. The liquid-chromatography device of claim 11 wherein the housing is formed of polymer or steel.

15. The liquid-chromatography device of claim 11 wherein the retention feature comprises a sleeve disposed on the proximal portion of the conduit.

16. The liquid-chromatography device of claim 15 wherein the sleeve comprises steel.

17. A kit having component parts capable of being assembled to form a reusable fitting for attaching a conduit to a port, the reusable fitting comprising:

a housing comprising a chamber and a ferrule portion at a proximal end of the housing;

a spring disposed inside the chamber;

a retainer disposed inside the chamber between a first end of the spring and the housing, the retainer formed as a single integral body and having a first opening for admitting a distal portion of a conduit and for admitting a retention feature fixed to a proximal end of the conduit to limit axial movement of the conduit in a distal direction, the retainer having an inner surface at a distal end of the retainer configured to engage the first end of the spring and having a slot at a proximal end of the retainer, a portion of the slot being aligned with the passage defined by the ferrule portion of the housing for receiving the conduit, the slot having a first inner surface that defines the first opening to receive the retention feature and a second inner surface that defines a second opening that is smaller than the first opening and sized to pass the conduit and impede the retention feature, the slot further including an off-center opening which is a radial extension in relation to the first and second inner surfaces; and a cap attached to a distal end of the housing and engaging the second end of the spring to urge the spring against the retainer to thereby urge the conduit in a proximal direction.

* * * * *